United States Patent [19]
Ide

[11] Patent Number: 5,995,218
[45] Date of Patent: Nov. 30, 1999

[54] METHOD FOR INSPECTING DEFECTS OF WAFER AND INSPECTION EQUIPMENT THEREOF

[75] Inventor: Takashi Ide, Tokyo, Japan

[73] Assignee: NEC Corporation, Tokyo, Japan

[21] Appl. No.: 09/007,757

[22] Filed: Jan. 15, 1998

[30] Foreign Application Priority Data

Jan. 17, 1997 [JP] Japan ..................................... 9-006442

[51] Int. Cl.$^6$ .................................................. G01N 21/00
[52] U.S. Cl. ..................................... 356/237.1; 356/239.1; 356/239.2; 356/239.7; 356/239.8; 356/237.3; 356/237.2
[58] Field of Search ............................. 356/237.1, 239.1, 356/239.2, 239.7, 239.8, 237.2, 237.3, 237.4, 237.5, 429, 430, 240, 426, 427, 428, 431, 369; 250/559.41, 559.48, 559.22, 559.45, 572, 562, 563

[56] References Cited

U.S. PATENT DOCUMENTS

| | | | |
|---|---|---|---|
| 4,342,515 | 8/1982 | Akiba et al. | 356/237 |
| 5,471,066 | 11/1995 | Hagiwara | 250/559.48 |
| 5,602,401 | 2/1997 | Broude et al. | 250/559.45 |
| 5,699,447 | 12/1997 | Alumot et al. | 382/145 |

FOREIGN PATENT DOCUMENTS

| | | |
|---|---|---|
| 61-279131 | 12/1986 | Japan . |
| 64-23144 | 1/1989 | Japan . |
| 6-213808 | 8/1994 | Japan . |

OTHER PUBLICATIONS

Testu Takahashi et al., "Study of nylon processing measurement on the surface of a silicon–wafer (Report No. 4)—detected pattern characteristics of a non–arrival corpuscle —", Paper presented at meeting of Japanese Precision Engineering Society, Spring, 1996, pp. 1118–1121.

*Primary Examiner*—Frank G. Font
*Assistant Examiner*—Michael P. Stafira
*Attorney, Agent, or Firm*—Young & Thompson

[57] ABSTRACT

A wafer defect detection apparatus includes a moving device for moving the wafer in a parallel direction to the wafer's surface, a light-emitting device for emitting an incident light on the surface of the wafer, a light-receiving device for receiving a reflected light reflected by the (111) crystal plane of the wafer, and a rotating device for rotating the wafer with respect to a line perpendicular to the wafer surface as a rotation axis, the [001] direction of the wafer being parallel to the normal line direction of the surface of the wafer. The light-emitting device is arranged in the direction tilted by $(57.7°-\alpha)$ from the rotation axis and the incident light impinges on the position where the rotation axis intersects the surface of the wafer. The light-receiving device is arranged in the direction tilted by $(54.7°+\alpha)$ in the direction same as that of the light-emitting device from the rotation axis, and the value of $\alpha$ is $-35.3°$ to $35.3°$ excluding $0°$.

19 Claims, 7 Drawing Sheets

METHOD FOR INSPECTING DEFECTS OF WAFER AND INSPECTION EQUIPMENT THEREOF

BACKGROUND OF THE INVENTION

1. Field of the Invention

The present invention relates to a method and the inspection equipment for inspecting defects of wafer suited for detecting a COP defect in a regular octahedral form surrounded by {111} crystal planes of grown-in defects, crystal defects in single crystal of silicon.

2. Description of the Related Art

For fine defects existing in a silicon single crystal produced by the Czochralski method (CZ method), a COP (Crystal Originated Particle) defect has been detected. The existence of the COP defect has been confirmed by detecting a pit formed in the silicon wafer by washing using the SC-1 liquid effective for removal of particles on the silicon wafer. However, since the size of the pit of the COP defect ranges from around 0.1 to 0.2 $\mu$m and the density of the COP defect in the crystal is as low as $1 \times 10^5$ to $1 \times 10^7$ (cm$^{-3}$), there are few cases in which the defect was directly observed. However, the form of COP in the silicon single crystal has been confirmed to be a microscopic regular octahedron surrounded with the {111} crystal planes.

The pit of the COP defect formed on the silicon wafer surface in this way has a fear of deteriorating pressure-resistance characteristics of the oxide film formed on the silicon wafer. In recent years, in the MOS device, as the number of bits increases, refinement and increased area of the chip have been promoted, and severity of the requirements for characteristics of gate oxide film further increases. Therefore, studies on Grown-in defects, crystal defects such as COP defects, etc., have been actively carried forward. Consequently, in order to study the COP defects, it is essential to detect defects such as the COP defects, etc with cerainty.

DESCRIPTION OF THE RELATED ART

Hitherto, semiconductor wafer defect detection methods or detection equipment thereof have been proposed (Japanese Non-examined Patent Publication No. Sho 61-279131, Japanese Non-examined Patent Publication No. Sho 64-23144). In the detection equipment recited in the Japanese Non-examined Patent Publication No. Sho 61-279131, a laser beam source for detecting foreign matter, a detector, and a laser beam source for removing the foreign matter are equipped. According to the defect detection equipment, it is possible to detect and remove the foreign matter dropping from a crystallization equipment by the vapor-phase approach during the epitaxial growth of a silicon film.

On the other hand, in the detection method recited in the Japanese Non-examined Patent Publication No. Sho 64-23144, it is possible to detect defects in an epitaxial layer thinner than the laser beam diameter by using laser beam and adjusting the incidence angle of the laser beam.

However, in the detection equipment recited in the Japanese Non-examined Patent Publication No. 61-279131, it is possible to detect foreign matter dropping from the crystallization equipment by the vapor-phase approach, but it is unable to detect the COP defect in the silicon single crystal produced by the CZ method. In the detection method recited in the Japanese Non-examined Patent Publication No. 64-23144, it is possible to detect the defect in the epitaxial layer thinner than the laser beam diameter but similarly, it is unable to detect the COP defect.

Therefore, the conventional method for detecting the COP defect employs a process comprising two stages as follows. First, the crystal defect and foreign matter, etc. on the surface or in the vicinity of the surface of the silicon wafer is detected by the use of a particle detection equipment (foreign matter detection equipment). Next, by observing the position where the crystal defect and foreign matter, etc. are detected by the particle detection equipment with an atomic force microscope (AFM), a scanning-type electron microscope (SEM), etc., it is judged whether what has been detected by the particle detection equipment is actually the COP defect or not. In the particle detection equipment, by irradiating the silicon wafer surface with light and detecting the scattered light caused by the foreign matter or defect, etc. against this irradiating light, the existence and the position of the foreign matter or defects are confirmed.

Because with the conventional detection method of COP defect, it is unable to judge what kind of defect the particle detected by the particle detection equipment is, the detected position must be observed using the atomic force microscope, etc. Consequently, it takes labor and time to move the silicon wafer from the particle detection equipment to the atomic force microscope, etc. In addition, after moving the silicon wafer, it need time to observe the silicon wafer again.

In Page 547 of Memoirs of Academic Lecture Meeting of the 1995 Fall Convention of Precision Engineering society (1995), a detection equipment for silicon wafer defect is recited. FIG. 1 schematically shows the conventional detection equipment recited in Page 547 of the Memoirs. In the conventional equipment recited in the reference, an object lens 52, a half mirror 53, and an Ar laser beam source 54 are arranged sequentially from a silicon wafer 51 side perpendicularly with respect to the silicon wafer 51 surface to be detected. An aperture, lenses, polarizers, and optical fibers, etc. (not shown) are arranged between the half mirror 53 and the Ar laser beam source 54. In the parallel direction to the silicon wafer 51 surface from the half mirror 53, a lens 55 and a CCD area sensor 56 are arranged. An aperture (not shown) is arranged between the half mirror 53 and the lens 55.

In the conventional detection equipment configured in this way, the Ar laser beam 57 emitted from the Ar laser beam source 54 is irradiated against the silicon wafer 51, and the reflected light 58 is received by the CCD area sensor 56. And by analyzing the intensity distribution of defect pattern of the reflected light 58, the particle diameter of the particle adhering to the silicon wafer 51 surface can be estimated.

However, even in the above-mentioned detection equipment, it is difficult to distinguish the COP defect from other defects.

SUMMARY OF THE INVENTION

An object of the present invention is to provide a method for inspecting when defects and the inspection equipment thereof that can accurately detect the COP defect in a short time which exists at the silicon wafer surface and in the vicinity of the surface and affects the pressure-resistance characteristics of the oxide film of the device.

The wafer defect inspection method related to the present invention comprises a step of detecting the existence of defects in wafer, a step of rotating the wafer or a light-emitting device with respect to a line passing through the defect and perpendicular to the surface of the wafer as a rotation axis while allowing an incident light to impinge on the defect from the light-emitting device, and a step of measuring changes of the intensity of a reflected light from the defect.

In the present invention, when the COP defect exists in the wafer, the intensity of the reflected light reflected from the COP defect or its pit in the form of a regular octahedron surrounded by the {111} crystal planes varies at specified intervals. Consequently, it is possible to distinguish the COP defect extremely easily from various other defects.

The wafer detection equipment related to the present invention comprises a moving device for moving a wafer parallel to the surface thereof, a light-emitting device for emitting an incident light on the surface of the wafer, a light-receiving device for receiving a reflected light of the incident light reflected by the (111) crystal plane of the wafer, and a rotating device for driving to rotate the wafer or the light-emitting device and the light-receiving device with the line perpendicular to the wafer surface as a rotation axis.

In the present invention, first, with the incident light emitted on the wafer surface by the light-emitting device, the wafer is moved in the direction parallel to the surface thereof by the moving device. In this event, if any COP defect or defects such as particles, etc. exist at the wafer surface, the incident light is reflected or scattered. If there is any light reflected from the (111) crystal plane, such reflected light is received by the light-receiving device. Then, with the defect irradiated with the incident light, for example, the wafer is rotated by a rotating device with respect to a line perpendicular to the surface as a rotation axis. With this, the intensity of the reflected light received by the light-receiving device varies. In particular, if the defect is the COP defect, the COP defect has a regular octahedral form surrounded by the {111} crystal planes, and therefore, the intensity of reflected light exhibits characteristic changes. With this, from various defects formed in the wafer, the COP defect is identified and detected. Instead of rotating the wafer, even if the light-emitting device and the light-receiving device are rotated, the COP defect can be identified and detected from intensity changes of the reflected light as in the case when the wafer is rotated. Consequently, the COP defect can be detected accurately and extremely easily without taking labor and time by using the atomic force microscope, etc.

DETAILED DESCRIPTION OF THE PREFERRED EMBODIMENTS

Figure 1:
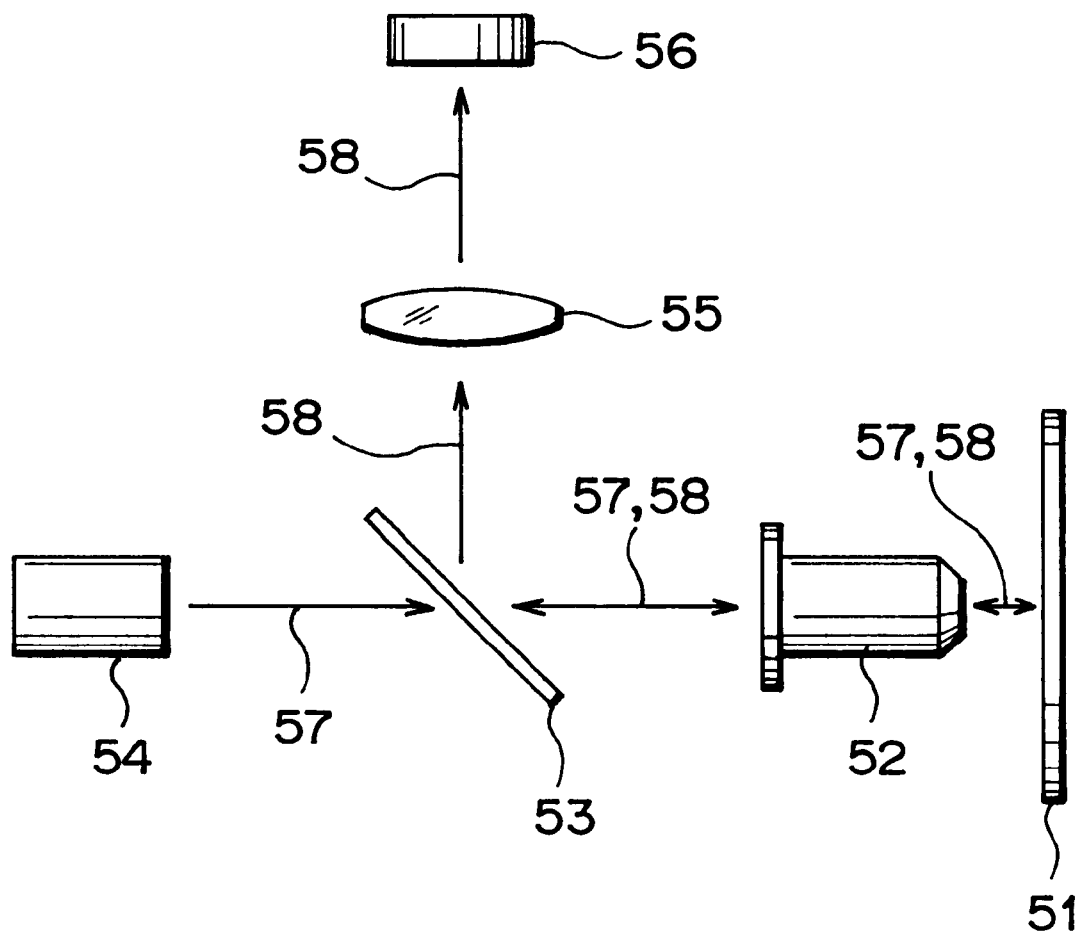
FIG. 1 is a schematic diagram showing a conventional defect detection equipment recited in Page 547 of the Memoirs of Academic Lecture Meeting of the 1995 Fall Convention of Precision Engineering Society (1995)
Figure 2:
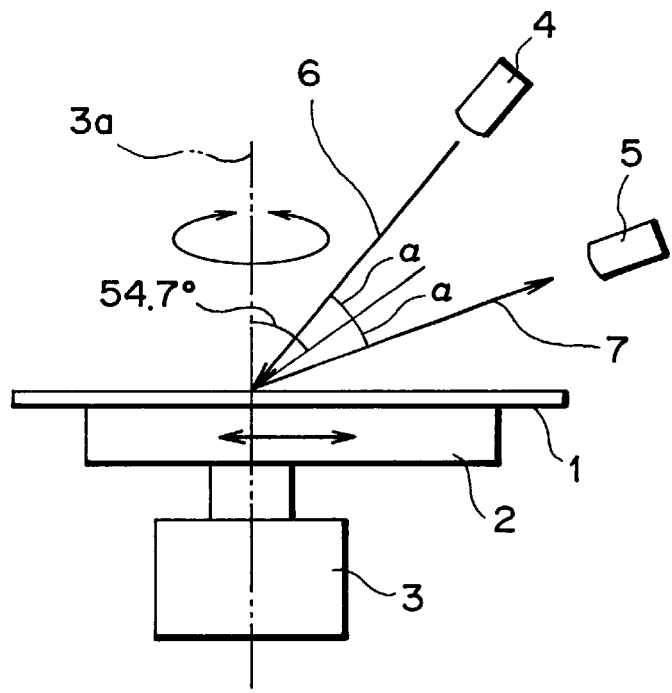
FIG. 2 is a schematic diagram showing an inspection equipment of wafer related to the first embodiment according to this invention.

Referring now to drawings, preferred embodiments of this invention will be specifically described. FIG. 2 is a schematic diagram showing an inspection equipment of wafer related to the first embodiment according to the invention. The silicon wafer 1 is mounted on an XY stage 2. The XY stage 2 can be moved in the X direction in the plane parallel to the surface of the silicon wafer 1 and in the Y direction crossing at right angles with the X direction in the same plane. The XY stage 2 is supported by the rotation stage 3 for rotating the XY stage 2 around the axis 3a perpendicular to the surface of the silicon wafer 1. The silicon wafer 1 is moved to the X direction or the Y direction by the XY stage 2, and an optional point on the silicon wafer 1 coincides with the point on the rotation center axis 3a of the rotation stage 3. With this configuration, the optional point on the silicon wafer 1 can be the rotation center. After the XY stage 2 is controlled to position the silicon wafer 1, the silicon wafer 1 is rotated by the rotation stage 3.

Above the XY stage 2, a light-emitting element 4 and a light-receiving element 5 are arranged. The light-emitting element 4 is arranged in the direction tilted by (54.7°−α) from the rotation center axis 3a, and the light is irradiated from the light-emitting element 4 to the position where the rotation center axis 3a intersects the silicon wafer 1 surface. On the other hand, the light-receiving element 5 is arranged in the direction tilted in the direction same as the light-emitting element 4 by the angle of (54.7°+α) from the rotation center axis 3a, and the reflected light reflected at the position where the rotation center axis 3a intersects the silicon wafer 1 surface is received by the light-receiving element 5. That is, the light emitted from the light-emitting element 4 impinges on the rotation center 9 of the silicon wafer 1 surface from the incidence direction 6, is reflected from the rotation center 9 of the silicon wafer 1 surface to the detection direction 7, and is received by the light-receiving element 5.

Figure 3:
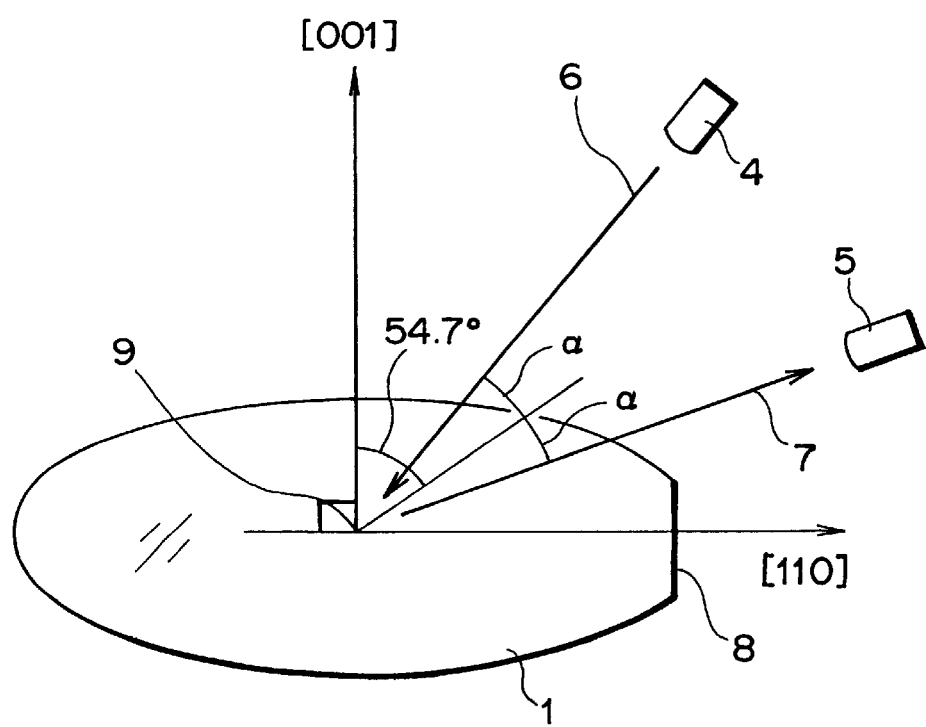
FIG. 3 is a schematic diagram showing the positional relation of the light-emitting element and light-receiving element against the silicon wafer in the wafer inspection equipment related to the first embodiment.

FIG. 3 is a schematic diagram showing the positional relation of the light-emitting element and the light-receiving element to the silicon wafer in the inspection equipment of wafer related to the first embodiment. As the silicon wafer 1, a (001) silicon wafer that is used for a general semiconductor integrated device is used, and the [001] direction of the silicon single crystal is parallel to a normal line direction of the silicon wafer 1. That is, the [001] direction of the silicon single crystal is aligned with a line drawn normal to the surface of silicon wafer 1. To the silicon wafer 1, an orientation flat 8 is formed for identifying the [110] direction of the silicon single crystal. In this embodiment, from the axis 3a to the [110] direction side of the silicon wafer 1, a light-emitting element 4 is arranged in the direction tilted by the angle of (54.7°−α) and a light-receiving element 5 is arranged in the direction tilted by the angle of (54.7°+α). And the light emitted from the light-emitting element 4 impinges on the rotation center 9 at (54.7°−α) with respect to the [001] direction, and is reflected at (54.7°+α) with respect to the [001] direction from the rotation center 9.

Figure 4:
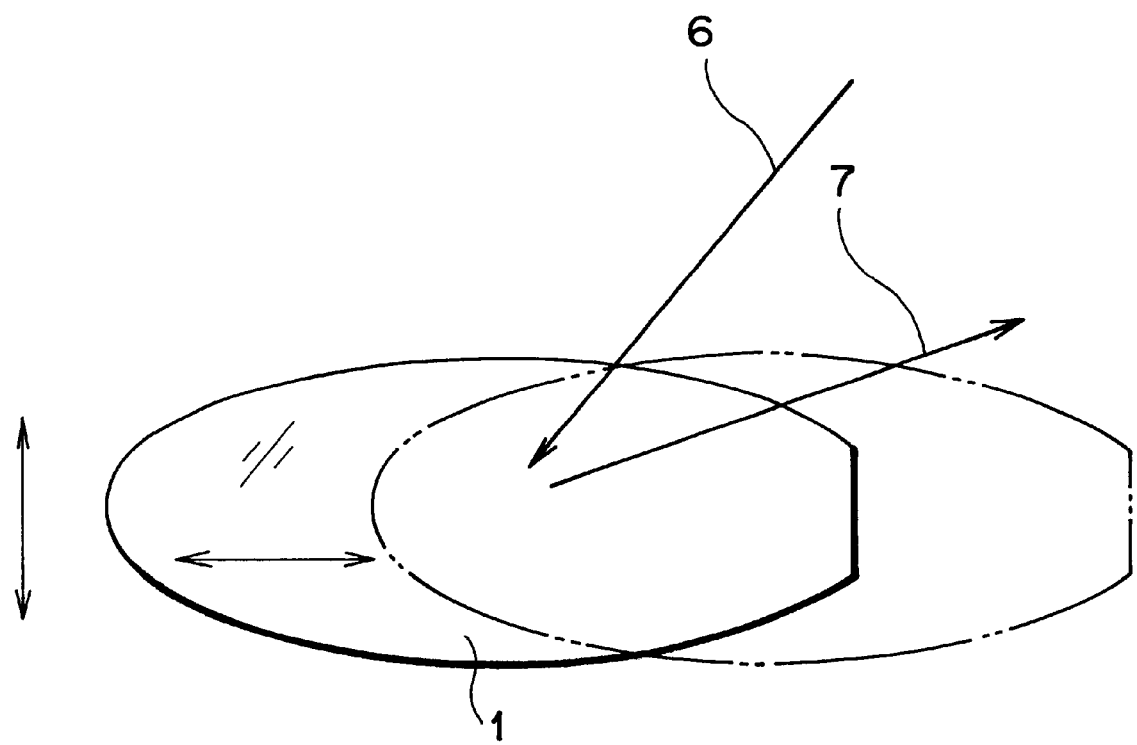
FIG. 4 is a schematic diagram showing the state of a silicon wafer moved by the XY stage.

Now, description will be made on the operation of the inspection equipment of wafer related to the first embodiment configured as described above. FIG. 4 is a schematic diagram showing the state in which the silicon wafer is moved by the XY stage. By the silicon wafer 1 being moved by the XY stage 2 in the direction parallel to the surface, an optional position on the silicon wafer 1 is irradiated with the light emitted from the light-emitting element 4. If a defect such as a particle or a pit which scatters the light is irradiated while the XY stage 2 is controlled to move the irradiated position on the silicon wafer 1, part of the light scattered by this defect advances to the direction shown in the detection direction 7. And by the light which advanced toward the detection direction 7 being received by the light-receiving element 5, the existence of the defect is detected. In the defects whose existence are detected by the light-receiving element 5, a pit generated by the COP defect may be included.

Figure 5:
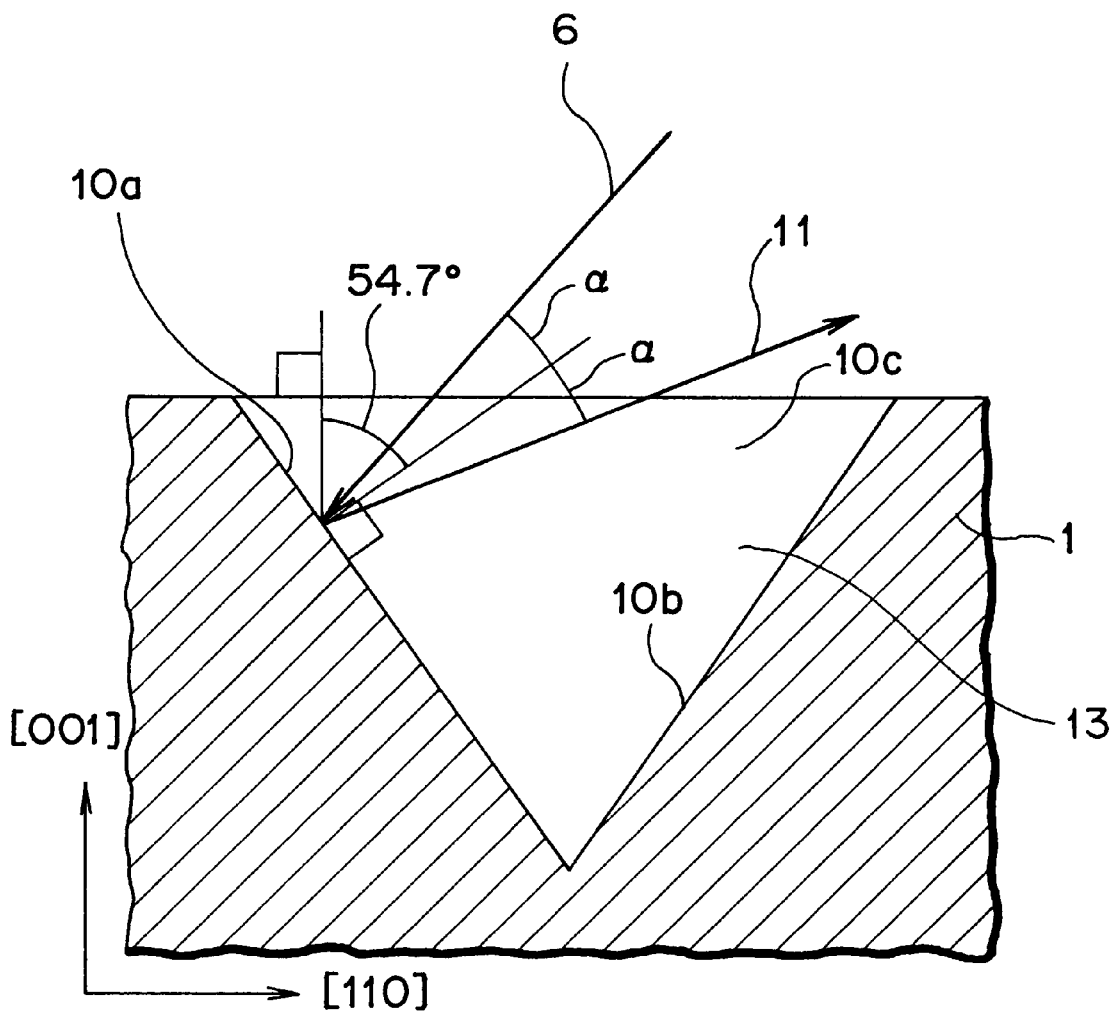
FIG. 5 is a schematic cross-sectional view in the ($1\overline{1}0$) crystal plane showing a pit of the COP defect formed on the silicon wafer.

FIG. 5 is a schematic cross-sectional view in the ($1\bar{1}0$) crystal plane showing a pit of the COP defect formed on the silicon wafer surface. As described above, since the COP defect is a regular octahedral form surrounded by the {111} crystal planes, the pit 13 of the COP defect forms a regular quadrangular pyramid with the {111} crystal planes as side faces. And the (111) crystal plane 10a, ($\bar{1}\bar{1}1$) crystal plane 10b, ($\bar{1}11$) crystal plane 10c, and ($1\bar{1}1$) crystal plane (not shown) which form side faces of the regular quadrangular pyramid are all regular triangles. Since the pit 13 of the COP defect is a regular quadrangular pyramid having four side faces of regular triangle, the angle formed by the normal line of the (111) crystal plane 10a, ($\bar{1}\bar{1}1$) crystal plane 10b, ($\bar{1}11$) crystal plane 10c, or ($1\bar{1}1$) crystal plane and the normal line of the silicon wafer 1 surface becomes 54.7°. Now, because as described above, the light-emitting element 4 is arranged in the direction tilted at an angle of (54.7°−α) in the [110] direction side of the silicon wafer 1 from the rotation center axis 3a, part of the light emitted from the light-emitting element 4 impinges on the (111) crystal plane 10a opposite to the light-emitting element 4 at an incidence angle α. And the light impinging on the (111) crystal plane 10a is reflected at the reflecting angle a by the (111) crystal plane 10a and the reflecting light advances in the reflecting direction 11. Because this reflecting direction 11 coincides with the detection direction 7, the reflected light by the (111) crystal plane 10a is received by the light-receiving element 5 and the existence of the defect is detected. When the incidence angle α exceeds 35.3°, the reflected light by the (111) crystal plane 10a impinges on the ($\bar{1}\bar{1}1$) crystal plane 10b, and therefore on the light-receiving element 5 side, the reflected light does not impinge. Consequently, in order to detect the pit 13 of the COP defect, the angle α must be less than 35.3°.

When the defect such as the particle or the pit on the silicon wafer 1 surface by the light-emitting element 4 as described above, the move of the XY stage 2 stops and the silicon wafer 1 is positioned with the defect irradiated by the light-emitting element 4. Because the position where the defect is detected in located on the rotation center 9 of the silicon wafer 1, the silicon wafer 1 is rotated by the rotation stage 3 around the position where the detected defect exists.

Figure 6:
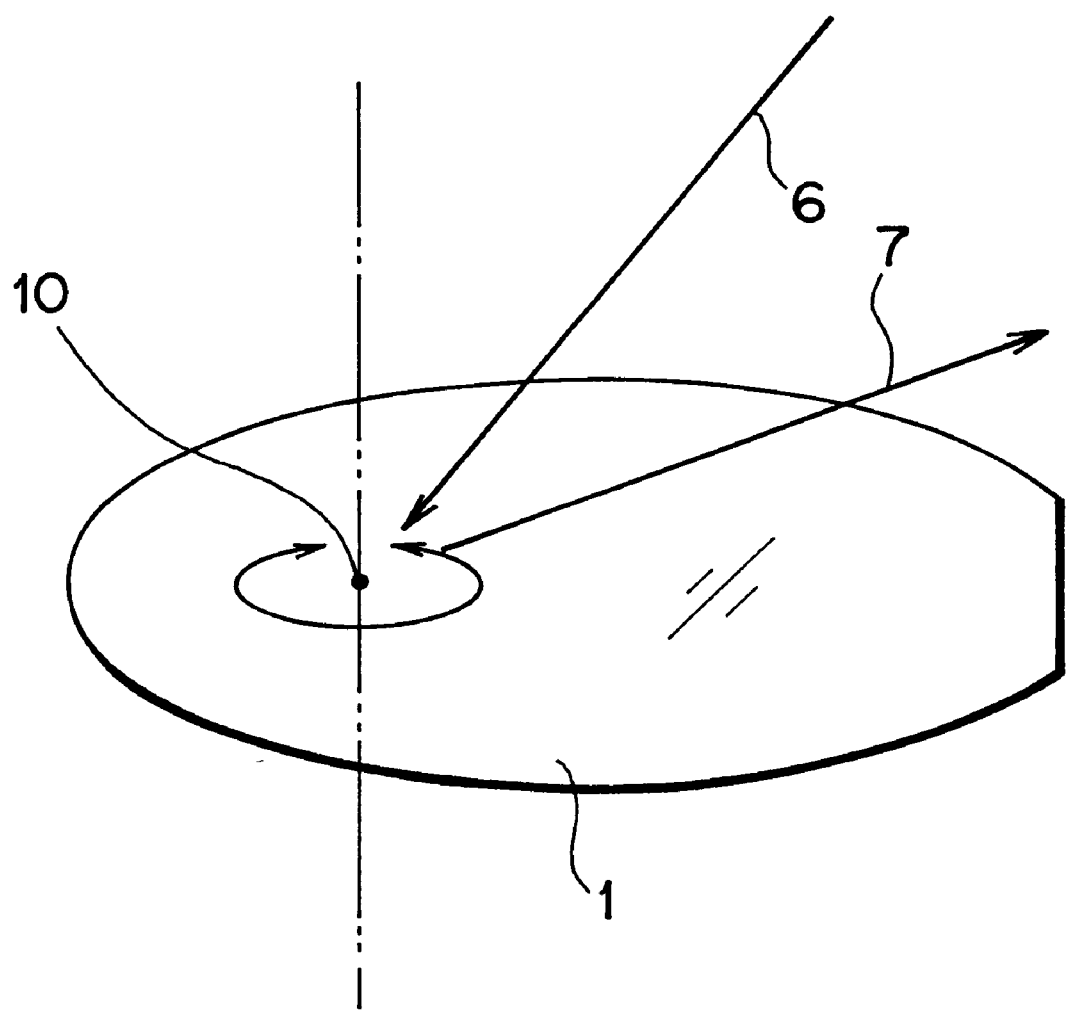
FIG. 6 is a schematic diagram showing the state of the silicon wafer rotated by the rotating stage.

FIG. 6 is a schematic diagram showing the state of the silicon wafer rotated by the rotation stage. As shown in FIG. 6, the silicon wafer 1 is rotated by the rotation stage 3 around the rotation center axis 3a passing the detection position 10 where the defect exists and perpendicular to the silicon wafer 1. In this event, to the defect on the silicon wafer 1 surface, the light from the light-emitting element 4 is irradiated, and the irradiated light is scattered or reflected by the defect. Part of the scattered or reflected light goes out to the detection direction 7 and is received by the light-receiving element 5. And there is a case in which the intensity of the light received by the light-receiving element 5 varies in accordance with the profile of the defect such as the particle or the pit, as the silicon wafer 1 is rotated and the defect is rotated.

Now description is made on the change in the intensity of the reflected light when the reflected light by the pit 13 of the COP defect is received by the light-receiving element 5. The pit 13 of the COP defect is a regular quadrangular pyramid comprising the (111) crystal plane 10a, ($\bar{1}\bar{1}1$) crystal plane lob, ($\bar{1}11$) crystal plane 10c and ($1\bar{1}1$) crystal plane as side faces as shown in FIG. 4. When the pit 13 is rotated by the operation of the rotation table 3, the pit 13 is rotated as if the bottom surface of the regular quadrangular pyramid rotates in the plane from the condition in which the incident light impinges on the (111) crystal plane 10a. Consequently, every time the pit 13 is rotated 90°, the light irradiated by the light-emitting element 4 impinges on any of the {111} crystal planes. Consequently, the intensity of the reflected light reflected from the four side faces of the regular quadrangular pyramid becomes the maximum at a 90° period of the rotation angle of the silicon wafer 1. That is, in the case of the COP defect, since the plane reflecting the light from the light-emitting element 4 is either one of the {111} crystal planes, the intensity of the reflected light from the COP defect becomes the maximum when the [110] direction, [$\bar{1}10$] direction, [$1\bar{1}0$] direction, or [$\bar{1}\bar{1}0$] direction of the silicon wafer 1 coincides with the direction which the [110] direction is directed under the condition before they are rotated while the silicon wafer 1 is being rotated. By measuring the changes in intensity of the reflected light by the {111} crystal planes, it is possible to identify whether the defect such as the particle or the pit reflecting the light is the pit of the COP defect or not.

As described above, when the intensity change of the reflected light received by the light-receiving element 5 varies at a 90° period as the silicon wafer 1 rotates, it is possible to judge that the defect is the pit of the COP defect. However, there is a case in which the foreign matter adhering to the silicon wafer 1 surface is a regular quadrangular pyramid. In such case, as is the case of the COP defect, rotating the silicon wafer while this adhesion is being irradiated with light may vary the intensity of the reflected light from the adhesion at a 90° period. However, almost all adhesions adhere without having any relationship with the crystal orientation, and it is quite rare that the (111) crystal plane of the adhesion becomes parallel to the (111) crystal plane of the COP defect. Consequently, when the XY stage 2 is moved to detect the pit of the COP defect, even if any adhesion having a profile similar to this kind of quadrangular pyramid or octahedron, etc., it is not confused with the pit of the COP defect.

In this way, according to this embodiment, it is possible to easily identify and detect the COP defect by detecting the existence of the defect such as the particle or the pit, rotating the silicon wafer 1 around the detected defect, receiving the reflected light from the defect of the light with which the rotation center of the silicon wafer 1 surface is irradiated, and investigating the dependency of the reflected light received on the rotation angle of the silicon wafer 1.

Figure 7A:
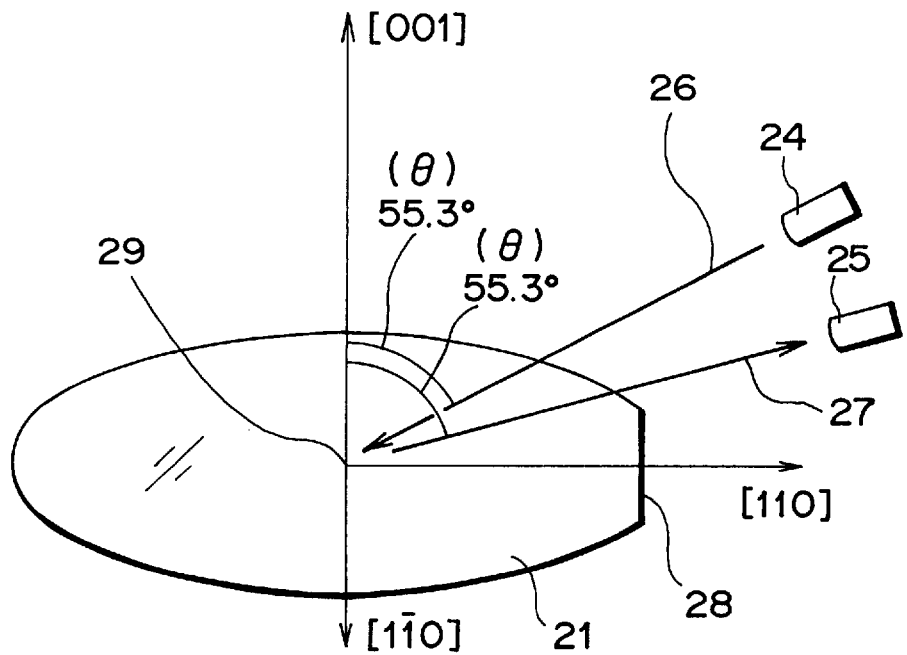
FIG. 7A is a schematic design showing the positional relation of the light-emitting element and the light-receiving element to the silicon wafer in the detection equipment of wafer related to the second embodiment according to this invention.
Figure 7B:
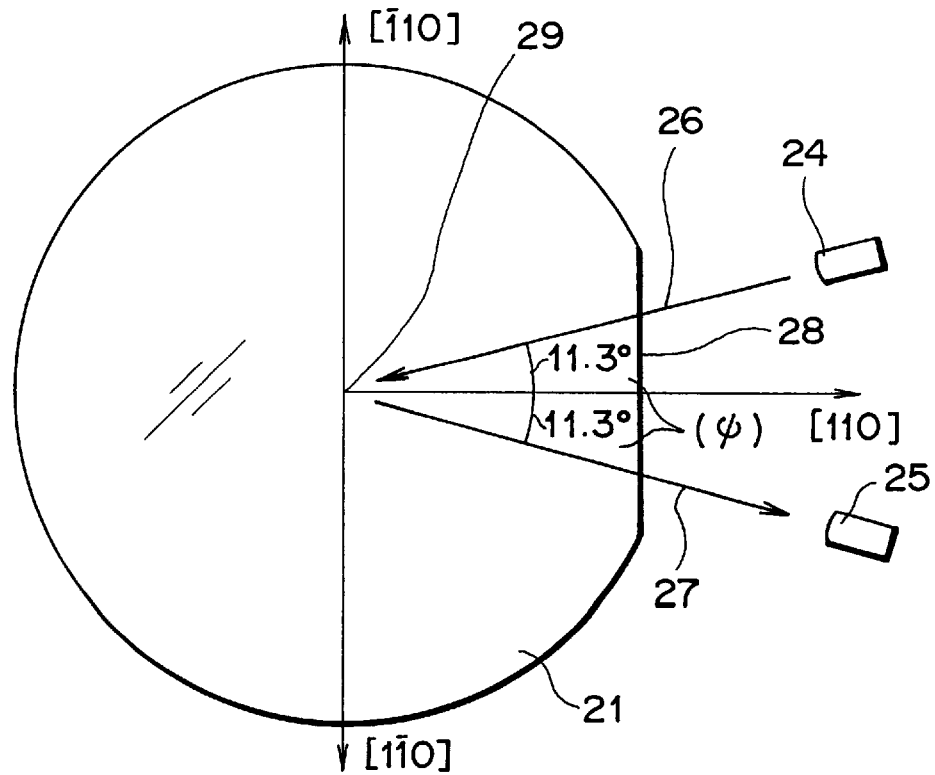
FIG. 7B is a schematic plan view of the same.

Next discussion will be made on the second embodiment according to the present invention. In the second embodiment, the positions the light-emitting element and the light-receiving element are arranged differ from those in the first embodiment. FIG. 7A is a schematic diagram showing the positional relationship of the light-emitting element and light-receiving element to the silicon wafer in the wafer detection equipment elated to the second embodiment according to this invention, and FIG. 7B is a schematic plan of the same. In the second embodiment as well, the XY stage and the rotation stage installed in the first embodiment are installed but, in FIG. 7A and 7B, the XY stage and the rotation stage are omitted.

In the embodiment, same as the first embodiment, a silicon wafer 21 is mounted and fixed on the XY stage (not shown), and the XY stage is moved in the direction parallel to the plane of the silicon wafer 21, and the silicon wafer 21 on the XY stage is moved. The XY stage is supported by the rotation stage (not shown) for rotating the XY stage around the perpendicular axis with respect to the surface of the silicon wafer 21. In this embodiment as well, the silicon wafer 21 is moved by the XY stage and an optional point on the silicon wafer 21 coincides with the point on the rotation center axis of the rotation stage. With this configuration, the optional point on the silicon wafer 21 can become the rotation center 29. After the XY stage is controlled to position the silicon wafer 21, the silicon wafer 21 is rotated by the rotation stage.

Next, the description will be made on the positional relationship of the light-emitting element and the light-receiving element to the silicon wafer 21. As shown in FIG. 7A and 7B, let the [001] direction of the silicon single crystal composing the silicon wafer 21 be parallel to the normal line direction of the silicon wafer 21 surface, i.e., normal to the silicon wafer 21 surface. To the silicon wafer 21, an orientation flat 28 is formed for identifying the [110] direction of the silicon single crystal. Above the silicon wafer 21, a light-emitting element 24 and a light-receiving element 25 are arranged. The light-emitting element 24 is arranged in the direction tilted by 55.3° from the rotation center axis of the rotation stage, and in the direction tilted by 11.3° from the straight line passing through the rotation center 29 and extending in the [110] direction as seen from the [001] direction of the silicon wafer 21. The light-receiving element 25 is arranged in the direction tilted by 55.3° from the rotation center axis of the rotation stage and in the direction tilted by 11.3° in the direction opposite to the light-emitting element 24 from the said straight line as seen from the [001] direction of the silicon wafer 21. The light emitted from the light-emitting element 24 impinges on the rotation center 29 of the silicon wafer 21 from the incidence direction 26, is reflected from the rotation center 29 to the detection direction 27, and is received by the light-receiving-element 25.

Next discussion will be made on the setting position of the light-emitting element 24 and the light-receiving element 25. The pit of the COP defect formed in the vicinity of the silicon wafer 21 surface has a general quadrangular pyramid with four equilateral triangles comprising {111} crystal planes of the silicon single crystal, and the light-emitting element 24 and the light-receiving element 25 arranged on the [110] direction side of the silicon wafer 21 face the (111) crystal plane. Now, when light impinges on the (111) crystal plane from the direction opposite to the [(1−x) (1+x) 1] direction tilted from an optional angle from the [111] direction which is a normal direction of the (111) crystal plane to the [−110] direction side, the incident light is mirror-reflected on the (111) crystal plane and advances in the [(1+x) (1−x) 1] direction. However, allow x to take an optional numerical value. In addition, the angles which the [(1−x) (1+x) 1] direction or [(1+x) (1−x) 1] direction makes with the [001] direction or [110] direction are equal, respectively.

Now let θ be the angle between the vector (1−x, 1+x, 1) and the vector (0, 0, 1), then, the relation of the following formula (1) holds for according to the Lambert's cosine law.

$$\cos\theta = 1/\sqrt{((1-x)^2+(1+x)^2+1)} = 1/\sqrt{(3+2x^2)} \quad (1)$$

Consequently, the following formula (2) is deduced.

$$\tan\theta = \sqrt{(2+2x^2)} \quad (2)$$

In addition, let ψ be the angle between the vector (1−x, 1+x, 0), which is the projected vector (1−x, 1+x, 1) on the (001) crystal plane, and the vector (1, 1, 0), then, the relation of the following formula (3) holds for according to the Lambert's cosine law.

$$\cos\psi = ((1-x)+(1+x))/(\sqrt{2}\times\sqrt{((1-x)^2+(1+x)^2+1)}) = 1/\sqrt{(1+x^2)} \quad (3)$$

Consequently, the following formula (4) is deduced.

$$\tan\psi = x \quad (4)$$

And the relation of $\tan^2\theta = 2\times(1+\tan^2\psi)$ results from the above formulae (2) and (4).

Because the vector (1−x, 1+x, 1) parallel to the advancing direction of incident light is the vector tilted from the [111] direction which makes the angle of 54.7° with the [001] direction to the [$\bar{1}$10] direction, the angle θ is greater than the angle 54.7° between the [111] direction and the [001] direction, and smaller than the angle 90° between the [$\bar{1}$10] direction and the [001] direction. On the other hand, the angle ψ between the incident light advancing direction as seen from the [001] direction side of the silicon wafer 21 and the [110] direction is 0° when θ=54.7°. And as the angle θ increases, it simply increases and the angle ψ becomes 90° when θ=90°. Consequently, the ranges of angles θ and ψ are 54.7°<θ<90° and 0°<ψ<90°, respectively. In the second embodiment, let x=0.2 and let θ=55.3° and ψ=11.3°.

Figure 8:
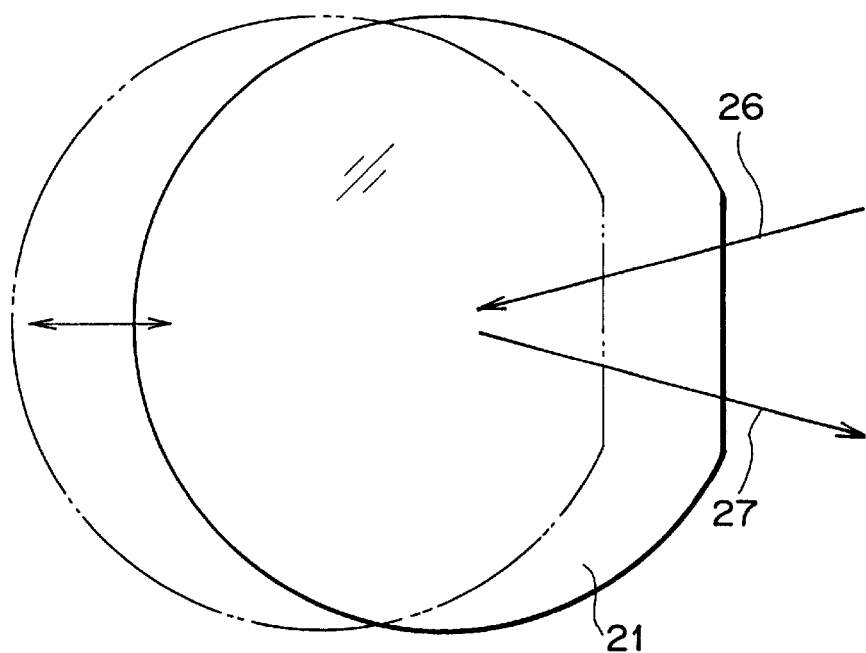
FIG. 8 is a schematic diagram showing the state of the silicon wafer moved by the XY stage.

Next description is made on the operation of the inspection equipment of wafer related to the second embodiment configured as described above. FIG. 8 is a schematic diagram showing the state in which the silicon wafer is moved by the XY stage. By shifting the silicon wafer 21 to the direction parallel to the plane by the XY stage (not shown), an optional position on the silicon wafer 21 is irradiated with the light emitted from the light-emitting element 24. If a defect such as a particle or a pit which scatters the light is irradiated while the irradiated position on the silicon wafer 21 is being shifted by controlling the XY stage, part of the light scattered by the defect advances to the detection direction 27. The existence of defect is detected by the light-receiving element 25 which receives the light advancing to the detection direction 27.

When the defect at the silicon wafer 21 surface is detected by the light-receiving element 24, the XY stage stops traveling and, with the defect irradiated by the light-emitting element 24, the silicon wafer 21 is positioned. Because the position where the defect is detected is located on the rotation center 29 of the silicon wafer 21, the silicon wafer 21 is rotated by the rotation stage around the position where the detected defect exists.

Figure 9:
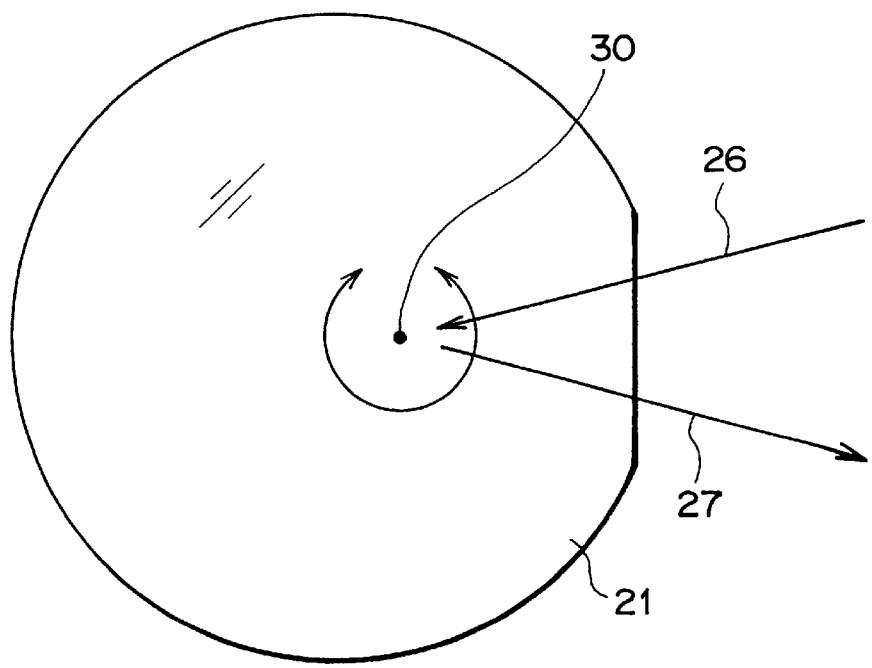
FIG. 9 is a schematic diagram showing the state of the silicon wafer rotated by the rotation stage.

FIG. 9 is a schematic diagram showing the state in which the silicon wafer is rotated by the rotation stage. The silicon wafer 21 is rotated by the rotation stage around the axis passing the detection position 30 where the defect exists and perpendicular to the silicon wafer 21. In this event, to the defect at the silicon wafer 21 surface, the light by the light-emitting element 24 is irradiated, and the irradiated light is dispersed or reflected. Part of the scattered or reflected light goes out in the detection direction 27 and is received by the light-receiving element 25. And there is a case in which the light intensity received by the light-receiving element 25 varies in accordance with the defect profile by rotating the defect.

Discussion is made on the change in the light intensity when the reflected light by the pit of the COP defect is received by the light-receiving element 25. The pit of the COP defect is a regular quadrangular pyramids comprising, for example, the (111) crystal plane, the ($\bar{1}$11) crystal plane, the ($\bar{1}$11) crystal plane, and the (1$\bar{1}$1) crystal plane as side faces as shown in FIG. 4. When the pit is rotated by the operation of the rotation stage, the pit is rotated in such a manner that the bottom face of the regular quadrangular pyramid rotated in the plane from the condition in which the incident light impinges on the (111) crystal plane. Consequently, every time the pit is rotated 90°, the light irradiated by the light-emitting element 24 impinges on any of the {111} crystal planes. Therefore, the intensity of the reflected light reflected from the four side faces of the regular quadrangular pyramid becomes the maximum at a 90° period of the rotation angle of the silicon wafer 21. That is, in the case of the COP defect, since the plane reflecting the light from the light-emitting element 24 is either one of the {111} crystal planes, the intensity of the reflected light from the COP defect becomes the maximum when the [1$\bar{1}$0] direction, the [$\bar{1}$10] direction, the [1$\bar{1}$0] direction, or the [$\bar{1}$$\bar{1}$0] direction of the silicon wafer 21 coincides with the direction which the [110] direction is directed under the condition before the silicon wafer 21 are rotated, while the silicon wafer 21 is being rotated. By measuring the changes in intensity of the reflected light by the {111} crystal planes, it is possible to identify whether the defect such as the particle or the pit reflecting the light is the pit of the COP defect or not.

As described above, when the intensity of the reflected light received by the light-receiving element 25 varies at a 90° period as the silicon wafer 21 rotates, it is possible to judge that the defect is the pit of the COP defect. However, there is a case in which the foreign matter adhering to the silicon wafer 21 surface is a quadrangular pyramid. In such case, as is the case of the COP defect, rotating the silicon wafer while this adhesion is being irradiated with light may vary the intensity of the reflected light from the adhesion at a 90° period. However, almost all adhesions adhere without having any relationship with the crystal orientation, and it is quite rare that the (111) crystal plane of the adhesion becomes parallel to the (111) crystal plane of the COP defect. Consequently, when the XY stage is moved to detect the pit of the COP defect, even if any adhesion having a profile similar to this kind of regular quadrangular pyramid or regular octahedron, etc., it is not confused with the pit of the COP defect.

In this way, according to this embodiment, it is possible to easily identify and detect the COP defect by detecting the existence of the defect such as the particle or the pit, rotating the silicon wafer 21 around the detected defect, receiving the reflected light from the defect of the light with which the rotation center of the silicon wafer 21 surface is irradiated, and investigating the dependency of the reflected light received on the rotation angle of the silicon wafer 21.

In the first and the second embodiments, the detection method of the pit of the COP defect formed at the silicon wafer surface has been described, but if the light reaches the COP defect in the regular octahedral form existing in the vicinity of the silicon wafer surface and the reflected light of this COP defect by the {111} crystal planes can be received, it is possible to detect the regular octahedral COP defect.

In the first and the second embodiments, Ar ion laser beams with wavelength from 351 nm to 364 nm are emitted from the light-emitting element. It is possible to use the light with short wavelength less than 500 nm in view of the pit size of COP defect which is as small as 0.1 to 0.2 μm.

It is also possible to detect the COP defect similarly when the wafer inspection equipment is configured with the arrangement of the light-emitting element and light-receiving element used in the first and the second embodiment replaced one another. Considering the case in which the arrangements of the light-emitting element and the light-receiving element are replaced, the range of the angle α shown in the first embodiment becomes $-35.3° < \alpha < 35.3°$ (where $\alpha \neq 0°$).

In addition, the inspection equipment of wafer according to the present invention shall not be limited to the arrangements of the light-emitting element and the light-receiving element shown in the first or the second embodiments. Irrespectively of the positions of the light-emitting element shown in the first or the second embodiments, the light-emitting element may be arranged at an optional position, the light is allowed to impinge on any of the {111} crystal planes of the COP defect at the silicon wafer surface from the light-emitting element, and the light-receiving element may be arranged in the reflection direction of the reflected light. In this case, the position of the light-receiving element should be decided in accordance with the position of the light-emitting element so that the intensity change of the reflected light resulting form the rotation of the silicon wafer can be measured.

Furthermore, the silicon wafer was rotated with the rotation stage as a rotating equipment in the first or the second embodiments, but COP defect may be detected as in the case of the first or the second embodiments by allowing the light-emitting and the light-receiving elements to be rotated with the line perpendicular to the silicon wafer surface as the rotation axis without using the rotation stage.

In the detection equipment of wafer according to the present invention, the COP defect in the regular octahedral form is subjected, but if the defect has some regularity in the form in addition to the regular octahedral form, and exhibit characteristics in the intensity change of the reflected light dependent on the profile, the detection equipment of wafer according to the present invention is applied and the defect can be detected.

What is claimed is:

1. A method for inspecting defects of a wafer comprising the steps of:

detecting the existence of a defect in said wafer;

rotating said wafer with respect to a line passing through said defect and perpendicular to the surface of said wafer as a rotation axis while allowing an incident light to impinge on said defect from a light-emitting device; and measuring changes of the intensity of a reflected light from said defect through a rotation of approximately 360°.

2. A method for inspecting defects of a wafer comprising the steps of:

detecting the existence of a defect in said wafer;

rotating a light-emitting device with respect to a line passing through said defect and perpendicular to the surface of said wafer as a rotation axis while allowing an incident light to impinge on said defect from said light-emitting device, and;

measuring changes of the intensity of a reflected light from said defects through a rotation of approximately 360°.

3. A method for inspecting defects of wafer according to claim 2, wherein the step of rotating said light-emitting device further comprises a step of rotating a light-receiving device for receiving said reflected light with respect to the line passing through said defects and perpendicular to the surface of said wafer as a rotation axis.

4. A method for inspecting defects of wafer according to claim 1, wherein the step of detecting the existence of said defects has a step of moving said wafer in the parallel direction to the surface thereof.

5. A method for inspecting defects of wafer according to claim 2, wherein the step of detecting the existence of said defects has a step of moving said wafer in the parallel direction to the surface thereof.

6. A method for inspecting defects of wafer according to claim 1, wherein the step of rotating said wafer has a step of allowing said incident light to impinge on the (111) crystal plane of said wafer.

7. A method for inspecting defects of wafer according to claim 2, wherein the step of rotating said wafer has a step of allowing said incident light to impinge on the (111) crystal plane of said wafer.

8. A method for inspecting defects of wafer according to claim 1, wherein the step of measuring the changes of the intensity of the reflected light from said defect has a step of receiving said reflected light from the (111) crystal plane of said wafer.

9. A method for inspecting defects of wafer according to claim 2, wherein the step of measuring the changes of the intensity of the reflected light from said defect has a step of receiving said reflected light from the (111) crystal plane of said wafer.

10. A method for inspecting defects of wafer according to claim 1, wherein the wavelength of said incident light is equal to or less than 500 nm.

11. A method for inspecting defects of wafer according to claim 2, wherein the wavelength of said incident light is equal to or less than 500 nm.

12. An inspection equipment of wafer comprising:
a moving device for moving a wafer in the parallel direction to the surface thereof;
a light-emitting device for emitting an incident light on the surface of said wafer;
a light-receiving device for receiving a reflected light reflected by the (111) crystal plane of said wafer during a rotation of approximately 360°; and
a rotating device for driving to rotate said wafer with respect to a line passing perpendicular through the surface of said wafer as a rotation axis.

13. An inspection equipment of wafer comprising:
a moving device for moving a wafer in the parallel direction to the surface thereof;
a light-emitting device for emitting an incident light on the surface of said wafer;
a light-receiving device for receiving a reflected light reflected by the (111) crystal plane of said wafer during a rotation of approximately 360°; and
a rotating device for driving to rotate said light-emitting device and said light-receiving device with respect to a line passing perpendicular through the surface of said wafer as a rotation axis.

14. An inspection equipment of wafer comprising:
a moving device for moving device for moving a wafer in the parallel direction to the surface thereof;
a light-emitting device for emitting an incident light on the surface of said wafer;

a light-receiving device for receiving a reflected light reflected by the (111) crystal plane of said wafer; and
a rotating device for driving to rotate said wafer with respect to a line passing perpendicular through the surface of said wafer as a rotation axis, wherein
the [001] direction of said wafer is aligned parallel to a normal line orthogonally contacting the surface of said wafer,
said light-emitting device is arranged in the direction tilted by (54.7°−α) from said rotation axis,
said incident light impinges on the position where said rotation axis intersects the surface of said wafer, and
said light-receiving device is arranged in the direction tilted by (54.7°+α) same as that of said light-emitting device, and
the value of α is −35.3° to 35.3° excluding 0°.

15. An inspection equipment of wafer comprising:
a moving device for moving a wafer in the parallel direction to the surface thereof;
a light-emitting device for emitting an incident light on the surface of said wafer;
a light-receiving device for receiving a reflected light reflected by the (111) crystal lane of said wafer; and
a rotating device for driving to rotate said light-emitting device and said light-receiving device with respect to a line passing perpendicular through the surface of said wafer as a rotation axis, wherein
the [001] direction of said wafer is aligned parallel to a normal ine orthogonally contacting the surface of said wafer,
said light-emitting device is driven to rotate in the direction tilted by (54.7°−α) from said rotation axis,
said incident light impinges on the position where said rotation axis intersects the surface of said wafer,
the light-receiving device is driven to rotate in the direction tilted by (54.7°+α) same as that of said light-emitting device, and
the value of α is −35.3° to 35.3° excluding 0°.

16. An inspection equipment of wafer comprising:
a moving device for moving a wafer in the parallel direction to the surface thereof;
a light-emitting device for emitting an incident light on the surface of said wafer;
a light-receiving device for receiving a reflected light reflected by the (111) crystal plane of said wafer; and
a rotating device for driving to rotate said wafer with respect to a line passing perpendicular through the surface of said wafer as a rotation axis, wherein
the [001] direction of said wafer is aligned parallel to a normal line orthogonally contacting the surface of said wafer,
said light-emitting device is arranged in the direction tilted by θ from said rotation axis,
said light-receiving device is arranged in the direction different from that of said light-emitting device and tilted by θ from said rotation axis,
the angle made by the line connecting said light-emitting device and said rotation axis and the line connecting said light-receiving device and said rotation axis is (2×ψ) as seen from the [001] direction of said wafer,
a formula $\tan^2\theta = 2 \times (1 + \tan^2\psi)$ holds,
the range of θ is 54.7° to 90°, and the range of ψ is 0° to 90°.

17. An inspection equipment of wafer comprising:

a moving device for moving a wafer in the parallel direction to the surface thereof;

a light-emitting device for emitting an incident light on the surface of said wafer;

a light-receiving device for receiving a reflected light reflected by the (111) crystal plane of said wafer; and a rotating device for driving to rotate said light-emitting device and said light-receiving device with respect to a line passing perpendicular through the surface of said wafer as a rotation axis, wherein the [001] direction of said wafer is aligned parallel to a normal line orthogonally contacting the surface of said wafer, said light-emitting device is driven to rotate in the direction tilted by θ from said rotation axis, said light-receiving device is driven to rotate in the direction different from said light-emitting device and tilted by θ from said rotation axis, the angle made by the line connecting said light-emitting device and said rotation axis and the line connecting said light-receiving device and said rotation axis is (2×ψ) as seen from the [001] direction of said wafer, a formula $\tan^2\theta = 2\times(1+\tan^2\psi)$ holds, the range of θ is 54.7° to 90°, and the range of ψ is 0° to 90°.

18. An inspection equipment of wafer according to claim 12, wherein the wavelength of said incident light is equal to or less than 500 nm.

19. An inspection equipment of wafer according to claim 13, wherein the wavelength of said incident light is equal to or less than 500 nm.

* * * * *